United States Patent [19]

Sung et al.

[11] Patent Number: 4,910,015
[45] Date of Patent: Mar. 20, 1990

[54] SURFACE-ACTIVE POLYSILOXANES AND DRUG RELEASING MATERIALS THEREOF

[75] Inventors: Cynthia Sung, Cambridge; Edward W. Merrill, Belmont, both of Mass.

[73] Assignee: Massachusetts Institute of Technology, Cambridge, Mass.

[21] Appl. No.: 110,006

[22] Filed: Oct. 19, 1987

[51] Int. Cl.$^4$ .............. A61K 31/74; A01J 21/00; A23G 1/00; B28D 7/20
[52] U.S. Cl. .................... 424/78; 424/81; 424/431; 424/432; 424/438; 424/449
[58] Field of Search ............... 424/78, 81, 431, 432, 424/438, 449

[56] References Cited

U.S. PATENT DOCUMENTS

| | | | |
|---|---|---|---|
| 4,423,099 | 12/1986 | Mueller et al. | 424/419 |
| 4,548,990 | 10/1985 | Mueller et al. | 424/81 |
| 4,624,848 | 11/1986 | Lee | 424/486 |
| 4,625,010 | 11/1986 | Hahn et al. | 528/31 |
| 4,666,745 | 5/1987 | Hahn et al. | 427/393.4 |
| 4,675,361 | 6/1987 | Ward, Jr. | 525/92 |
| 4,684,709 | 8/1987 | Ona et al. | 528/15 |
| 4,686,137 | 8/1987 | Ward, Jr. | 428/290 |

FOREIGN PATENT DOCUMENTS 002519 6/1979 European Pat. Off. .

OTHER PUBLICATIONS

R. W. Pekala, "Synthesis and Characterization of Polyether/Polysiloxane Networks for Blood-Interfacing Applications".
S. Hosaka et al., *J. Appl. Polym. Sci.*, 23, 2089-2098 (1979).
R. W. Pekala et al., *J. Colloid & Interface Sci.*, 101, 120-128.
R. W. Pekala et al., *Biomaterials*, 7, 372-378 (1986).
A. S. Hoffman, "Polymers in Medicine and Surgery", (Plenum Press, New York 1974), 33-44.
R. W. Pekala et al., *Biomaterials*, 7, 379-385 (1986).
B. Kanner et al., *Industrial and Engineering Chemistry Product Research and Development*, 6(2), 88-92 (1967).
R. langer, *Chem. Eng. Commun.*, 6, 1-48 (1980).
S. Wisniewski et al., *J. Membr. Sci.*, 6, 299-308 (1980).
J. M. Anderson et al., *ACS Symposium Series*, 31, 167-179 (1976).
M. P. Embrey et al., *Brit. Med. J.*, 28, 901-902 (1980).
C. T. Reinhart et al., *J. Membr. Sci.*, 18, 227-239 (1984).
B. K. Davis, *Proc. Natl. Acad. Sci., U.S.A.*, 71, 3120-3123 (1974).
Y. W. Chien, *ACS Symposium Series*, 33, 53-71 (1976).
T. J. Roseman et al., *ACS Symposium Series*, 33, 33-52 (1976).
S. Yolles, "Polymers in Medicine and Surgery", R. L. Kronenthal et al., eds. (Plenum Press, New York 1975), 245-261.
Pekala et al., *Biomaterials* 7: 372-378 (1986).

*Primary Examiner*—John Kight
*Assistant Examiner*—Carlos Azpuru
*Attorney, Agent, or Firm*—Hamilton, Brook, Smith & Reynolds

[57] ABSTRACT

A crosslinked polymer network comprising the reaction product of a polyethylene oxide and a polyglycidoxypropylsiloxane is described. These materials form hydrogel networks having very high partition coefficients for selected pharmaceuticals and are suitable for controlled drug release and water purification.

37 Claims, 1 Drawing Sheet

SURFACE-ACTIVE POLYSILOXANES AND DRUG RELEASING MATERIALS THEREOF

BACKGROUND OF THE INVENTION

Controlled drug release formulations offer several advantages over conventional dosage forms. They can provide more stable systemic drug concentrations, eliminating periods of toxic or sub-therapeutic levels. Release rates can be set by the polymer structure of the polymeric release formulation, its geometry and its interactions with drugs. Less effect from environmental variations is found from patient to patient. Bioavailability usually is increased because the drug in the polymer is protected from degradation by the body's clearance mechanisms. Furthermore, problems related to poor patient compliance are reduced because the patient does not have to take the drug as often.

Numerous investigations have been carried out on drug release from both hydrophobic and non-degradable polymers containing uniformly distributed drug. Silicone rubber (the common name for crosslinked polydimethylsiloxane) is one of the more commonly studied materials because acute tissue inflammation to filler-free silicone implants is very mild. For example, silicone has been used for release of steroids, hydrophobic drugs which easily permeate through silicone. (see Y. W. Chien, *ACS Symposium Series*, 33, 53–71 (1976).) Steroid release rates in humans were constant up to 18 days. This phenomenon was attributed to rapid permeation of the steroids through the matrix compared to diffusion of drug through a boundary layer at the surface. As the equilibrium concentration of a compound in silicone was increased relative to the equilibrium concentration of the aqueous solution, the in vitro release rate approached zero-order. (See T. J. Roseman, et al., *ACS Symposium Series*, 33, 33–52 (1976).

Other hydrophobic polymers that have been used for drug release include polyethylene and polethylenevinyl acetate (polyEVA). Polyethylene films have been used for release of progesterone in rabbits. (see S. Yolles, *Polymers in Medicine and Surgery*, R. L. Kronenthal, et al., eds., (Plenum Press, New York 1975), 245–261.) In this case, release rates declined rapidly during the first 14 days, the maintained a steady level to 39 days. The copolymer polyEVA has been used to release a variety of proteins. In these polymers, interconnecting pores were created by the initially solid drug particles dispersed in the matrix. Drug release occurred when water diffused into the pores and dissolved the proteins and the protein then diffused through the water phase to the surface. (see R. Langer, *Chem. Eng. Commun.*, 6, 1–48 (1980).)

Hydrophilic polymers also have been studied as drug releasing materials. Polyhydroxyethylmethacrylate (polyHEMA) is the most popular material for studying drug release because of its ease of synthesis and its biocompatibility which has been demonstrated through its widespread use as soft contact lenses. Partition and diffusion coefficients of inorganic salts add hydrophilic non-electrolytes in loosely (1%) crosslinked gels have been measured. (see S. Wisniewski, et al., *J. Membr. Sci.*, 6, 299–308 (1980).) These compounds partitioned mainly in the bulk water of the gel therefore implying that diffusion occurred in the bulk water phase. PolyHEMA gels have also been used for release of hydrophobic compounds. (see J. M. Anderson. et al., *ACS Symposium Series*, 31, 167–179 (1976).)

Other hydrophilic polymers that have been used for drug release include polyethylene oxide (PEO)-polyurethane, polyvinyl alcohol((PVA), polyacrylamide, and a multi-polymeric system of methacrylate, ethacrylate and N-vinylpyrrolidone. (see M. P. Embrey, et al., *Brit. Med. J.*, 28, 901–902, (1980); C. T. Reinhart, et al., *J. Membr. Sci.*, 18, 227–239 (1984); B. K. Davis, *Proc. Natl. Acad. Sci., U.S.A.*, 71, 3120–3123, (1974); S. Hosaka, et al., *J. Appl. Polym. Sci.*, 23, 2089–2098, (1979). For example, PEO-polyurethane was used for nearly constant release of prostaglandin $E_2$ for 10 hours. In the multipolymeric system, the composition of the polymer was varied to obtain networks of varying swelling ratios. Continuous release of erythromycin from these networks for four days was obtained.

Preparation of crosslinked materials by the reaction of polypropylene glycol (PPG) with polyglycidoxypropylmethylsiloxane (PGPMS) was described by Pekala et al. (J. Colloid & Interface Sci. 101, 1984, 120–8; Biomaterials, 7, 1986, 372–8). These crosslinked materials were synthesized for studying the blood compatibility of these materials.

Despite these previous findings, a need still exists for a material having a balance of hydrophobic and hydropilic properties suitable for continuous pharmaceutical delivery.

SUMMARY OF THE INVENTION

The invention pertains to polymer networks which comprise the reaction product of a polyethylene oxide (PEO) and a glycidoxypropylsiloxane polymer (PGPS) and hydrogels thereof. Surprisingly, these materials have been found to have very high partition coefficients for various materials. The high partition coefficients of selected drugs in these materials make them very suitable for applications such as the controlled release of pharmaceuticals into patients over an extended period of time. The high partition coefficients of these materials also make them suitable for the treatment or purification of water. A further advantage of these materials is their biocompatibility as several decades of clinical experience with silicone rubber implants have established that issue reaction to this material is very mild.

DETAILED DESCRIPTION OF THE INVENTION

Figure 1:
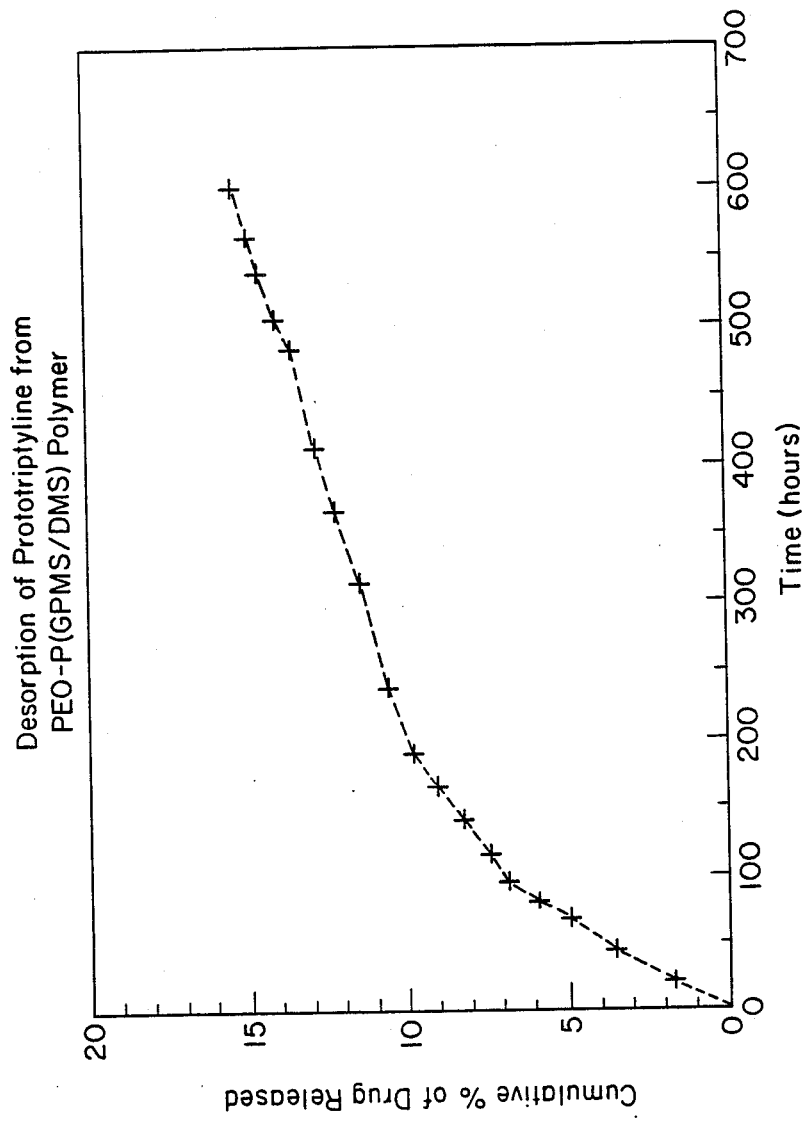
FIG. 1 is a plot of cumulative drug release by desorption versus time for protriptyline incorporated into a crosslinked networksynthesized from PEO and P(GPMS/DMS).

This invention involves the synthesis and use of crosslinked polymer networks comprising the reaction product of a glycidoxypropylsiloxane polymer (PGPS) and a polyethylene oxide (PEO).

The PGPS materials described herein comprise chain polysiloxanes containing the structural units (A) and (B) as represented by Formula (1) below:

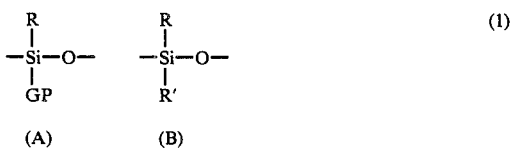

(1)

(A)  (B)

wherein GP is a glycidoxypropyl unit, and R and R' are —CH$_3$, —C$_2$H$_5$ or phenyl. Each PGPS molecule has between 3 and 25 (A) units, and the ratio of the number of (B) units to the number of (A) units is no greater than 10:1.

As used herein, the term polyethylene oxide (PEO) is defined to include the class of polymers characterized by repeat units of the form (OCH$_2$CH$_2$). One such compound is α,ω dihdroxy PEO characterized by hydroyl units at each terminal. In other PEO varieties, either one of the hydroxyl units can be replaced by a methyl group such as in polyethylene glycol monomethyl ether, or by an ethyl group such as in polyethylene glycol monoethyl ether. Alteratively, either or both of the hydroxyl groups can be placed by an amino group such as in α,ω diamino PEO. Other end capping groups for PEO are also known in the art.

The glycidoxypropyl (GP) units of this polymer are represented by Formula (2) below:

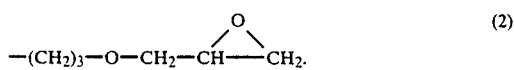

(2)

Representative siloxane polymers of this invention include polyglycidoxypropylmethylsiloxane, (PGPMS), and poly(glycidoxypropylmethylsiloxane/-dimethylsiloxane), P(GPMS/DMS), copolymer. These materials are among those represented by general Formula (1) above and the abbreviation PGPS.

These siloxane polymers, existing as oily liquids similar to silicone oil, have been found to spontaneously emulsify water, whereas polydimethylsiloxane (PDMS) by itself does not. Additionally, when immersed in aqueous solutions, PGPS and network sof PEO and PGPS absorb compounds much more readily than either PEO or PDMS alone, thereby allowing these siloxane materials to act as excellent vehicles for applications such as the controlled release of pharmaceuticals.

When immersed in water, the reaction product of PEO and PGPS materials form a material known as a hydrogel. The term "hydrogel" refers to a broad class of polymeric materials which are swollen extensively in water but which do not dissolve in water. Generally, hydrogels are formed by polymerizing a hydrophilic monomer in an aqueous solution under conditions in which the polymer becomes crosslinked so that a three-dimensional polymer network sufficient to gel the solution is formed. Hydrogels are described in greater detail in Hoffman, A. S., "Polymers in Medicine and Surgery", Plenum Press, New York, pp. 33–44 (1974), the teachings of which are incorporated herein by reference.

To form the crosslinked polymer networks of this invention, PEO is dissolved in an organic solvent for both PEO and PGPS. PEO-PGPS material are synthesized by mixing PGPS into the PEO solution, followed by the dropwise addition of a ring-opening Lewis-acid catalyst such as dilute boron-trifluoride etherate. Other suitable catalysts include BCl$_3$, AlCl$_3$, SbF$_3$, SbF$_5$, SbCl$_5$. Exclusion of water is essential for the reaction of the PEO and PGPS to proceed properly. This may be accomplished by adding a drying agent such as molecular sieves, calcium hydride or calcium chloride to the solution, thereby removing trace amounts of water. The reacting solution is stirred and transferred to molds which are maintained under a saturated atmosphere of solvent for at least 8 hours. The polymer samples are then dried to effect the removel of the organic solvent.

Alternatively, a network an be formed by the reaction of a PGPS and α, ωdiamino PEO. In this case, the PGPS and the α,ω diamino PEO are dissolved in an organic solvent. Rather than adding a catalyst, the reaction mixture is heated to increase the rate of reaction. The polymer network product is then dried to effect the removal of the organic solvent.

The synthesis of the preferred PGPMS materials is done by adding allyl glycidyl ether to polyhydromethylsiloxane (PHMS) via a catalyzed reaction. While catalysts such as rhodium and iridium may be used, platinum is preferred. Similarly, P(GPMS/DMS) is synthesized by starting with the PHMS/PDMS copolymer. A more detailed discussion of the synthesis of these preferred PGPMS compounds is described by Pekala, et al. (*J. Colloid & Interface Sci.* 101, 1984, pp. 120–128; and *Biomaterials*, 7, 1986, pp. 372–378) the teachings of which are hereby incorporated by reference.

A representative synthesis of this invention is given in Formula (3) below in which α,ω dihydroxy PEO and a PGPS chain are contacted with boron trifluoride catalyst in a dichloromethane medium.

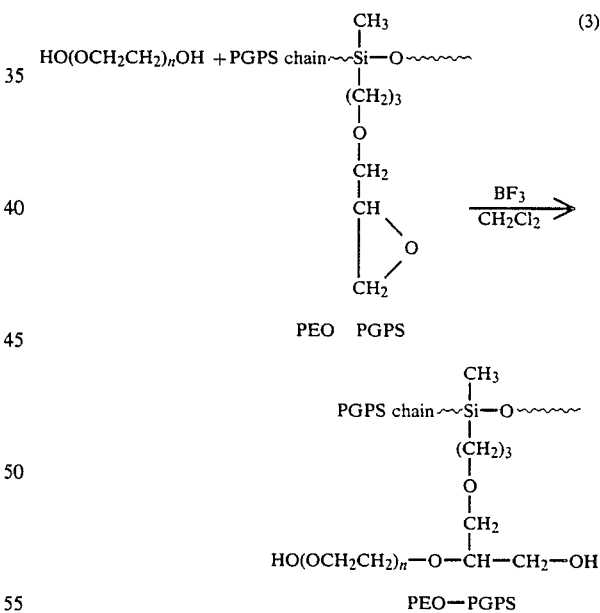

(3)

In Formula 3, n is between about 25 and about 500. In the preferred embodiment, n is greater than about 38. The mole ratio of glycidoxypropyl groups to hydroxyl groups in the initial mixture should be greater than 1:2 and preferably greater than 1:1. In a preferred embodiment, the mole ratio of glycidoxypropyl groups to hydroxyl groups is 3:2 or greater.

Emulsification properties of the PGPS precursor of the networks described herein can be illustrated in the following manner. An aliquot of water is gently layered upon the top of an aliquot of PGPS. Initially, two distinct and clear liquids are observed. Spontaneously, the interface between the polymer phase and the aqueous phase becomes progressively diffractive of light as a result of emulsification of water in polymer and vice versa. When an aliquot of water is mixed vigorously with an aliquot of liquid PGPS, three distinct phases form: the lowest phase being an emulsion of water in polymer, the middle phase being an emulsion of polymer in water, and the top phase being a clear aqueous solution. The emulsion is extremely stable and centrifugation at 9000 G for 30 minutes does not separate the polymer from water.

The partition coefficient K is defined as the ratio of the concentration of a compound dissolved in a hydrogel network or polymer to the concentration of compound dissolved in the non-hydrogel or -polymer phase at equilibrium when he hydrogel network or polymer is immersed in an aqueous mixture in which a solute has been dissolved.

To determine K in the case wherein the polymer is in liquid form, an aliquot or aqueous solution of a compound of known concentration is thoroughly mixed with an aliquot of polymer. The two phases are allowed to reach equilibrium, and the concentration of solute in the aqueous phase is measured. K can be determined by a mass balance on the aqueous phase using equation (2) below:

$$K = (C_i/C_f - 1)(V_a/V_p) \quad (2)$$

wherein $C_i$ is the initial concentration of the solute in the aqueous solution, $C_f$ is the final concentration of the solute in the aqueous solution once mixed with the polymer and allowed to reach equilibrium, $V_a$ is the volume of the aqueous phase and $V_p$ is the volume of the polymer phase.

K may also be determined when the polymer is an insoluble, crosslinked network such as a hydrogel. In this case, the network may undergo swelling depending upon the content and molecular weight of the PEO in the network. To find K, polymer which has reached its equilibrium swollen state is placed in a solution in which tee initial solution volume and solute concentration are known. Once the mixture reaches equilibrium, the concentration of the aqueous phase is remeasured. By using an appropriate mass balance, K can be calculated. This mass balance is given below as equation (3):

$$K = \frac{V_a(C_i/C_f - 1)}{V_p + V_s} \quad (3)$$

wherein $C_i$ and $C_f$ are as stated previously, $V_a$ is the initial volume of the aqueous solution, $V_s$ is the volume of aqueous solution in swollen polymer, and $V_p$ is the initial polymer volume.

The high partitioning of these hydrogels makes them an excellent delivery vehicle for pharmaceuticals, especially those having low molecular weight and limited solubility in water and with which it is desirable to dispense in substantially constant, low dosages over an extended period of time. One such pharmaceutical class is that of tricyclic antidepressants. Another pharmaceutical for which the hydrogel network is an excellent delivery vehicle is leutinizing hormone release hormone (LHRH).

Tricyclic antidepressants are prescribed for endogenous depression, a condition thought to be caused by a defect in the uptake of amine neurotransmitters at the presynaptic junctions. The tricyclic antidepressants benefit from a controlled delivery formulation for a number of reasons. Depressed patients are at a higher risk for suicide, and thus more likely to hoard the drug and then attempt to take an overdose. Furthermore, tricyclic antidepressants have a long induction period, sometimes taking several weeks before patients obtain relief from the drug. As a result of the long induction period, patients often stop using the medication after a short period of time because they think it is not working. A controlled delivery form of the drug solves these problems by providing continuous release of the drug for the time period necessary to provide relief.

Additionally, many patients who respond to tricyclic antidepressants are much more likely to avoid a relapse if they are maintained on the drug. However, patient compliance to long-term drug regimens is generally very poor. This problem is also eliminated with controlled release drug formulations.

Representative examples of tricyclic antidepressants are shown below.

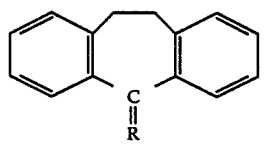

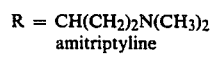
R = CH(CH$_2$)$_2$N(CH$_3$)$_2$
amitriptyline

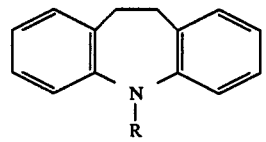

R = (CH$_2$)$_3$N(CH$_3$)$_2$
imipramine

R = (CH$_2$)$_3$NHCH$_3$
desipramine

R = CH$_2$CH(CH$_3$)CH$_2$N(CH$_3$)$_2$
trimipramine

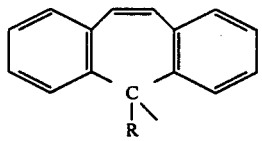

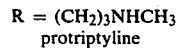
R = (CH$_2$)$_3$NHCH$_3$
protriptyline

Crosslinked polymer networks have been found to have unexpectedly high partition coefficients for compounds such as tricyclic antidepressants.

Tables 1 to 3 below show partitioning data obtained for several compounds when contacted with polymers, or polymer networks of PDMS, P(GPMS/DMS) and PEO. The data of Tables 2 and 3 show that it is possible to control partitioning via network composition.

In each case shown in the tables, the drug was dissolved in a phosphate buffered saline solution (pH 7.4) and subsequently contacted with the polymer phase. Both dissolving and contacting steps were carried out at room temperature. In Tables 2 and 3, the PEO- P(GPMS/DMS) networks are in their swollen hydrogel form.

TABLE 1
Partition Coefficients in PDMS, Unreacted P(GPMS/DMS), Crosslinked P(GPMS/DMS) Networks, and Crosslinked PEO Networks

| Drug | K in PDMS | K in Unreacted P(GPMS/DMS) | K in Crosslinked P(GPMS/DMS) | K in Crosslinked PEO |
|---|---|---|---|---|
| Protriptyline | 0.4 | 29 | 34 | 2 |
| Desipramine | 0.4 | 22 | 43 | 2 |
| Imipramine | 21 | 139 | 123 | 2 |
| Amitriptyline | 68 | 281 | 296 | 2 |
| Trimipramine | 155 | 465 | 565 | 2 |

TABLE 2
Partitioning of Protriptyline in PEO-P(GPMS/DMS) Hydrogel Networks

| M.W. of PEO | % PGPMS | K |
|---|---|---|
| 1700 | 35 | 69 |
| 1700 | 42 | 146 |
| 1700 | 50 | 224 |
| 2600 | 40 | 252 |
| 8600 | 35 | 64 |
| 8600 | 50 | 258 |
| 17700 | 20 | 37 |
| 17700 | 35 | 94 |
| 17700 | 50 | 221 |

TABLE 3
Partitioning of Desipramine in PEO-P(GPMS/DMS) Hydrogel Networks

| M.W. of PEO | % PGPMS | K |
|---|---|---|
| 1700 | 50 | 42 |
| 2600 | 40 | 52 |
| 8600 | 35 | 67 |
| 8600 | 50 | 76 |
| 17700 | 35 | 54 |
| 17700 | 50 | 72 |

As shown in Table 1, protripyline illustrates the unexpected properties of P(GPMS/DMS), networks made from POO, and networks made from P(GPMS/DMS). Partitioning of protriptyline into P(GPMS/DMS) ($K=29$) is markedly higher than its partitioning into PDMS alone ($K=0.4$). Protrityline does not appreciably absorb into radiation crosslinked PEO ($K=2$) when compared to its absorption into crosslinked P(GPMS/DMS) ($K=34$).

Significantly, the amount of protriptyline incorporated is greater in PEO-P(GPMS/DMS) hydrogel networks compared to any of the polymers individually. (See Tables 2 and 3). Drug absorption is thus likely to occur specifically in the interfacial region between the two polymer phases. PEO likely plays an important role in the partitioning of compounds in the PPEO-P(GPMS/DMS) networks by imparting swellability to these polymers, thereby allowing the aqueous solution to penetrate into the polymer.

Materials of the type described herein have many useful applications. For example, if a compound partitions highly into the PEO-PGPS network, the network may be used for the slow continuous release of a pharmaceutical as described previously. Another application is for the use of the PEO-PGPS network to remove high partitioning compounds from aqueous solutions, such as in the removal of compounds from waste water.

These are just two examples of the applications for the polymers and hydrogel networks described herein and are not intended to limit the scope of the invention.

The invention is further and more specifically illustrated by the following examples.

EXAMPLE 1

Production of PEO-P(GPMS/DMS) Networks 20 g of PEO, nominal degree of polymerization of 45, was dissolved in 100 ml of dichloromethane. To remove trace water from this solution, 20 g of 3A molecular sieve was added to this solution and vigorously stirred for 12 hours. Under nitrogen, the solution was then filtered through a 0.5 micron filter. The final PEO concentration of this solution was measured by gel permeation chromatography (GPC) using differential refractometry detection. A similar procedure was carried out for P(GPMS/DMS), nominal degree of polymerization of 12: 20 g of P(GPMS/DMS) was dissolved in 100 ml of dichloromethane. The solution was dried with 3A molecular sieves, stirred, filtered and analyzed by GPC under the same conditions as used with PEO described above.

A reaction between PEO and P(GPMS/DMS) was carried out under an atmosphere of nitrogen. A volume of PEO solution containing 0.5 PEO and a volume of P(GPMS/DMS) solution containing 0.5 g P(GPMS/DMS) were mixed together, and a volume of dichloromethane was added so that the final total polymer concentration was 18.5%. An aliquot of boron trifluoride etherate was diluted 140 times in dichloromethane and 2 ml of this diluted catalyst was added dropwise and stirred into the polymer solution. Aliquots of solution were transferred into polyethylene molds and placed in a sealed container which contained a saturated atmosphere of dichloromethane. After 15 hours, the sample was removed and placed in a vacuum apparatus for complete removal of dichloromethane.

0.5 g of the resulting crosslinked PEO-P(GPMS/DMS) network was mixed with 20.0 ml of a 1.0 millimolar protriptyline solution in phosphate buffer (pH 7.4). After thorough stirring, the concentration of protriptyline in the remaining solution and in the initial solution was measured by liquid chromatography using a C18-silia column with ultraviolet detection at a wavelength of 254 nm. The partition coefficient K was calculated using Equation (2) (given previously) and found to be 224.

EXAMPLE 2

Continuous Release of a Protriptyline From a PEO-P(GPMS/DMS) Network 0.6 g of a PEO-P(GPMS/DMS) network ($K=224$) comprising 50% PEO (molecular weight 1770), was placed in 20 ml of 1.0 millimolar protriptyline solution in osphate buffer (pH 7.4). At equilibrium, the polymer had removed 98.4 of the protriptyline in solution. The polymer was then transferred into 20 ml of phosphate buffer (pH 7.4) and the concentration of protriptyline released from the sample was measured with time. After each measurement, the polymer was transferred to 20 ml of fresh phosphate buffer. FIG. 1 plots the cumulative percentage of protriptyline released by desorption from a PEO-P(GPMS/DMS) network over a 600 hour period.

EXAMPLE 3

Synthesis of Crosslinked Network Derived from Reaction of P(GPMS/DMA) and α,ω-diamino Polyethylene Oxide 0.5 g α,ω-diamino polyethylene oxide, nominal degree of polymerization of 45, and 0.5 g P(GPMS/DMS), degree of polymerization of 12, were dissolved in 5 ml toluene. The solution was heated to 35° C. and maintained at that temperature in a closed container for fifteen hours. The crosslinked polymer was then transferred to a vacuum apparatus for complete removal of toluene.

It should be noted that this reaction can proceed in the absence of a catalyst, however, to obtain gelling in a short time (i.e., less than one day), the reaction mixture must be heated. The solvent toluene was substituted for dichloromethane, because toluene has a higher boiling point that dichloromethane, therefore making it easier to use at the elevated reaction temperature.

EQUIVALENTS

Those skilled in the art will know, or be able to ascertain using no more than routine experimentation, many equivalents to the specific embodiments expressly described herein. These are intended to be within the scope of the invention as described by the claims herein.

We claim:

1. A crosslinked polymer network comprising the reaction product of a polyethylene oxide and a glycidoxypropylsiloxane having between 3 and 25 glycidoxypropyl units per molecule.

2. A crosslinked polymer network as in claim 1 further having a pharmaceutical incorporated into the network.

3. A crosslinked polymer network as in claim 2 wherein the pharmaceutical is a tricyclic antidepressant.

4. A crosslinked polymer network as in claim 3 wherein the tricyclic antidepressant is selected from the group consisting of protriptyline, amitriptyline, trimipramine, imipramine, and desipramine.

5. A crosslinked polymer network as in claim 2 wherein the pharmaceutical is leutinizing hormone release hormone.

6. A crosslinked polymer network as in claim 1 wherein the glycidoxypropylsiloxane is polyglycidoxypropylmethylsiloxane.

7. A crosslinked polymer network as in claim 1 wherein the glycidoxypropylsiloxane is a poly(glycidoxypropylmethlysiloxane/dimethylsiloxane) copolymer.

8. A crosslinked polymer network as in claim 1 wherein the polyethylene oxide is selected from the group consisting of dihydroxy polyethylene oxide, polyethylene glycol monomethyl ether, polyethylene glycol monothyl ether, monoamino polyethylene oxide, and diamino polyethylene oxide.

9. A crosslinked polymer network comprising a polyglycidoxypropylsiloxane having between 3 and 25 glycidoxypropyl units per molecule crosslinked with polyethylene oxide, produced by the method comprising the steps of:
   (a) mixing polyethylene oxide and a polyglycidoxypropylsiloxane having between 3 and 25 glycidoxypropyl units per molecule in solvent to form a reaction mixture;
   (b) adding a Lewis acid catalyst to the reaction mixture;
   (c) allowing the mixture to react to form a crosslinked network; and,
   (d) removing solvent from the product, thereby producing a crosslinked polyethylene oxide/polyglycidoxypropylsiloxane material.

10. A polymer network as in claim 9 wherein the polyglycdoxypropylsiloxane is polyglycidoxypropylmethylsiloxane.

11. A polymer network as in claim 9 wherein the polyglycidoxypropylsiloxane is poly(glycidoxypropylmethlsiloxane/dimethysiloxane) copolymer.

12. A polymer network as in claim 9 wherein the polyethylene oxide is selected from the group consisting of dihydroxy polyethylene oxide, polyethylene glycol monomethyl ether and polyethylene glycol monoethyl ether.

13. A polymer network as in claim 9 wherein the solvent is dichloromethane.

14. A polymer network as in claim 9 wherein the Lewis acid catalyst is selected from the group consisting of $BF_3$, $BC_3$, $AlCl_3$, $SbF_3$, $SbF_5$, and $SbCl_5$.

15. A polymer network as in claim 9 wherein the solvent is removed from the product polymer by drying.

16. A crosslinked polymer network comprising a polyglycidoxypropylsiloxane having between 3 and 25 glycidoxypopyl units per molecule crosslinked with a polyethylene oxide selected from the group consisting of monoamino polyethylene oxide and diamino polyethylene oxide, the crosslinked polymer network produced by the method comprising:
   (a) mixing the polyethylene oxide and polyglydicoxypropylsiloxane having between 3 and 25 glycidoxypropyl units per molecule in solvent to form a reaction mixture;
   (b) heating the reaction mixture;
   (c) allowing the mixture t react to form a cross-linked network; and,
   (d) removing solvent from the product, thereby producing a crosslinked polyethylene oxide/polyglycidoxypropylsiloxane material.

17. A polymer network as in claim 16 wherein the polyglycidoxypropylsiloxane is polyglycidoxypropylmethylsiloxane.

18. A polymer network as in claim 16 wherein the polyglycidoxypropylsiloxane is poy(glydicoxypropylmethylsiloxane/dimethysiloxane) copolymer.

19. A polymer network as in claim 16 wherein the solvent is toluene.

20. A polymer network as in claim 16 wherein the reaction mixture is heated to a temperature of about 35° C.

21. A polymer network as in claim 16 wherein the solvent is remove by vacuum drying.

22. A method for the controlled release of pharmaceuticals comprising the steps of:
   (a) providing a crosslinked polyethylene oxidepolyglycidoxypropylsiloxane network wherein the polyglycidoxypropylsiloxane is poly glycidoxypropylmethylsiloxane having between 3 and 25 glycidoxypropyl units per molecule,
   (b) contacting the crosslinked network with a solution containing a pharmaceutical;
   (c) allowing the pharmaceutical to incorporate into the crosslinked network;

(d) contacting the pharmaceutical-containing network with the body fluids of a patient; and, (e) allowing the pharmaceutical-containing network to release the pharmaceutical into the patient over an extended period of time.

23. A method as in claim 26 wherein the polyglycidoxypropylsiloxane is poly(glycidoxypropylmethylsiloxane/dimethylsiloxane) copolymer having between 3 and 25 glycidoxypropyl units per molecule.

24. A method as in claim 22 wherein the polyethylene oxide is selected from tee group consisting of dihydroxy polyethylene oxide, polyethylene glycol monomethyl ether, polyethylene glycol monoethyl ether, monoamino polyethylene oxide and diamino polyethylene oxide.

25. A method as in claim 22 wherein the pharmaceutical is a tricyclic antidepressant.

26. A method as in claim 25 wherein the tricyclic antidepressant is selected from the group consisting of protriptyline, amitriptyline, trimipramine, imipramine and desipramine.

27. A method as in claim 22 wherein the pharmaceutical is leutinizing hormone release hormone.

28. A hydrogel comprising an aqueous solution and the reaction product of polyethylene oxide and a glycidoxypropylsiloxane having between 3 and 25 glycidoxypropyl units per molecule.

29. A hydrogel as in claim 28 wherein the aqueous solution contains a pharmaceutical.

30. A hydrogel as in claim 28 wherein the pharmaceutical is a tricyclic antidepressant.

31. A hydrogel as in claim 28 wherein the tricyclic antidepressant is selected from the group consisting of protriptyline, amitriptyline, trimipramine, imipramine, and desipramine.

32. A hydrogel as in claim 28 wherein the pharmaceutical is leutinizing hormone release hormone.

33. A hydrogel as in claim 28 wherein the glycidoxypropylsiloxane is polyglycidoxypropylmethylsiloxane.

34. A hydrogel as in claim 28 wherenn the glycidoxypropylsiloxane is a poly(glycidoxypropylmethylsiloxane/dimethylsiloxane) copolymer.

35. A hydrogel as in claim 28 wherein the polyethylene oxide is selected from the group consisting of dihydroxy polyethylene oxide, polyethylene glycol monomethyl ether, polyethylene glycol monoethyl ether, monoamino polyethylene oxide, and diamino polyethylene oxide.

36. The emulsion produced by contacting a polyglycidoxypropylsiloxane having between 3 and 25 glycidoxypropyl units per molecule with an aqueous solution.

37. A crosslinked polymer network comprising the reaction product of a polyethylene oxide and a polyglycidoxypropylsiloxane having between about 3 and 25 glycidoxypropyl units per molecule.

* * * * *

UNITED STATES PATENT AND TRADEMARK OFFICE
CERTIFICATE OF CORRECTION

PATENT NO. : 4,910,015

DATED : March 20, 1990

INVENTOR(S) : Cynthia Sung and Edward W. Merrill

It is certified that error appears in the above-identified patent and that said Letters Patent is hereby corrected as shown below:

Column 9, Claim 8, line 58, change "monothyl" to ---monoethyl---;

Column 10, Claim 10, line 9, change "polyglycdoxyproplsiloxane" to ---polyglycidoxypropylsiloxane---;

Column 10, Claim 14, line 23, change "BC$_3$" to ---BCl$_3$---;

Column 10, Claim 16, line 29, change "glycidoxypopyl" to ---glycidoxypropyl---;

Column 10, Claim 16, line 40, change "t" to ---to---;

Column 10, Claim 18, line 49, change "poy(glydicoxypropyl-" to ---poly(glydicoxypropyl- ---; and Column 11, Claim 24, line 11, change "tee" to ---the---.

Signed and Sealed this

Thirteenth Day of August, 1991

Attest:

HARRY F. MANBECK, JR.

*Attesting Officer*     *Commissioner of Patents and Trademarks*